United States Patent [19]
Bruce et al.

[11] Patent Number: 5,679,867
[45] Date of Patent: Oct. 21, 1997

[54] CARBONYLATION VIA SOLID ACID CATALYSIS

[75] Inventors: David Alan Bruce, Greenville, S.C.; Mario L. Occelli, Atlanta, Ga.; David Anthony Schiraldi, Charlotte, N.C.; Dhiraj Sudesh Sood, Atlanta, Ga.; Cindy Elyse Sullivan, Madison, Wis.; Mark Gilmore White, Woodstock, Ga.

[73] Assignee: Hoechst Celanese Corporation, Somerville, N.J.

[21] Appl. No.: 611,446

[22] Filed: Mar. 1, 1996

[51] Int. Cl.$^6$ .................................................. C07C 45/49
[52] U.S. Cl. .................... 568/428; 502/214; 502/232; 502/263; 423/306; 423/69
[58] Field of Search ............... 568/428; 502/214, 502/232, 263; 423/306, 69

[56] References Cited

U.S. PATENT DOCUMENTS

| | | | |
|---|---|---|---|
| 2,485,237 | 10/1949 | Gresham et al. | 260/599 |
| 3,369,048 | 2/1968 | Hamilton et al. | 260/599 |
| 3,948,998 | 4/1976 | Fujiyama et al. | 260/599 |
| 4,218,403 | 8/1980 | Vanderpool | 568/428 |
| 4,554,383 | 11/1985 | Knifton | 568/428 |

FOREIGN PATENT DOCUMENTS

1128966  10/1968  United Kingdom.

OTHER PUBLICATIONS

"Formulation of Aromatic Compounds with CO in $HSO_3F$–$SbF_5$ under Atmospheric Pressure", *J. Org. Chem.* 57 (1992) 2677–2680.

"Researachers vie for cheapest TPA route", *Chemical Week*, Oct. 13, 1976, pp. 67–68.

"Superacid–Catalyzed Formulation of Aromatics with Carbon Monoxide", *J. Org. Chem.*, 50 (1985) 1483–1485.

*Journal of Organometallic Chemistry*, 194 (1980) 221–228.

"Make PTAL from CO and toluene", *Hydrocarbon Processing*, Nov. 1978, pp. 147–149.

*Primary Examiner*—José G. Dees
*Assistant Examiner*—Sreeni Padmanabhan
*Attorney, Agent, or Firm*—Robert H. Hammer, III; Miles B. Dearth

[57] ABSTRACT

The present invention is directed to a process for the carbonylation of an arylene to an arylaldehyde (e.g., toluene to tolualdehyde) in the presence of a solid acid catalyst. The process for making tolualdehyde comprises carbonylating toluene in the presence of either carbon monoxide or a source of carbon monoxide and in contact with a solid acid catalyst. The reaction is carried out at a temperature ranging from −40° to 200° C., and at a pressure ranging from 20–4000 psig.

25 Claims, 1 Drawing Sheet

CARBONYLATION VIA SOLID ACID CATALYSIS

FIELD OF THE INVENTION

This invention is directed to a process for the carbonylation of an arylene to an arylaldehyde (e.g., toluene to tolualdehyde) using a solid acid catalyst.

BACKGROUND OF THE INVENTION

A commercial process for the carbonylation of toluene to tolualdehyde has been sought as a method for reducing the cost of raw materials for making polyethylene terephthalate. "Researchers vie for cheapest TPA route", *Chemical Week*, Oct. 13, 1976, p. 67–68. To date, however, no commercially viable process has been found. The principal drawback associated with the previously disclosed processes has been the use of strong acid catalysts which are difficult to contain economically. Processes using these strong acid catalysts must be contained within process equipment made of expensive alloys. These alloys drive up the capital cost of the process, and thereby reduce its economic viability.

For example, U.S. Pat. No. 3,369,048 discloses the carbonylation (i.e. Gatterman-Koch reaction) of an arylene to an arylaldehyde (e.g. toluene to tolualdehyde), in a heterogeneous system, with carbon monoxide, a solid porous crystalline aluminosilicate catalyst, and hydrogen chloride (Column 2, lines 14–18 and Column 12, lines 33–58). The carbon monoxide and hydrogen chloride are added to the reactant in equimolar amounts (Column 13, lines 9–25). This process, however, requires the use of gaseous hydrogen chloride, a highly corrosive agent that can only be handled, on a commercially viable basis, utilizing expensive alloys.

Other previously disclosed carbonylation processes have utilized the Gatterman-Koch reaction mechanism, a variation of the Friedel-Crafts reaction mechanism.

Each of the following reactions is conducted in a homogenous system and utilizes a strong acid catalyst. The strong acid catalysts are: hydrogen chloride—aluminum trichloride/cuprous chloride (Gatterman, L., et al., *Chem. Ber.*, 30 (1987), 1622); hydrogen fluoride-boron trifluoride (U.S. Pat. Nos. 2,485,237 and 3,948,998, and "Make PTAL from CO and toluene", *Hydrocarbon Processing*, November 1978, pp. 147–149); hydrohalic acid—antimony pentahalide (Great Britain No. 1,128,966); hydrogen chloride-crystalline aluminosilicates (U.S. Pat. No. 3,369,048); hydrogen chloride—CuCl(PPh$_3$)$_n$, n=1 or 3 (Toniolo, L., et al., *Journal of Organometallic Chemistry*, 194 (1980) 221–228); hydrogen fluoride—tantalum, niobium, or antimony pentafluoride (U.S. Pat. No. 4,218,403); CF$_3$SO$_3$H+HF+BF$_3$ & CF$_3$SO$_3$H+SbF$_5$ (Olah, G. A., et al., "Superacid-Catalyzed Formulation of Aromatics with Carbon Monoxide", *J. Org. Chem.*, 50 (1985) 1483–1485); N-alkyl pyridinium halide and an anhydrous aluminum halide (U.S. Pat. No. 4,554,383); and HSO$_3$F+SbF$_5$ (Tanaka, M., et al., "Formulation of Aromatic Compounds with CO in HSO$_3$F-SbF$_5$ under Atmospheric Pressure", *J. Org. Chem.* 57 (1992) 2677–2680).

Accordingly, there still exists a need for a commercial carbonylation process for the manufacture of an arylaldehyde (e.g. tolualdehyde from toluene). Such a process would utilize a strong acid catalyst which could be easily handled without the need to employ expensive alloys for reaction containment.

SUMMARY OF THE INVENTION

The present invention is directed to a process for the carbonylation of an arylene to an arylaldehyde (e.g., toluene to tolualdehyde) in the presence of a solid acid catalyst. The process for making tolualdehyde comprises the steps of carbonylating toluene, in a heterogeneous system being essentially free of hydrogen chloride; with either carbon monoxide or a source of carbon monoxide; and in contact with a solid acid catalyst: capable of sorbing 1) at least 0.01 micro mole (mmole) pyridine/gram of catalyst on Brönsted acid sites and 2) at least 0.01 mmole pyridine/gram of catalyst on Lewis acid sites; and having 3) a metal promoter adapted for activating the carbon monoxide or the source of carbon monoxide; and a surface area of greater than 10 m$^2$/g. Additionally, the process is conducted at a temperature ranging from about –40° C. to about 200° C., and at a pressure of about 20 psig to about 4000 psig.

DETAILED DESCRIPTION OF THE INVENTION

Figure 1:
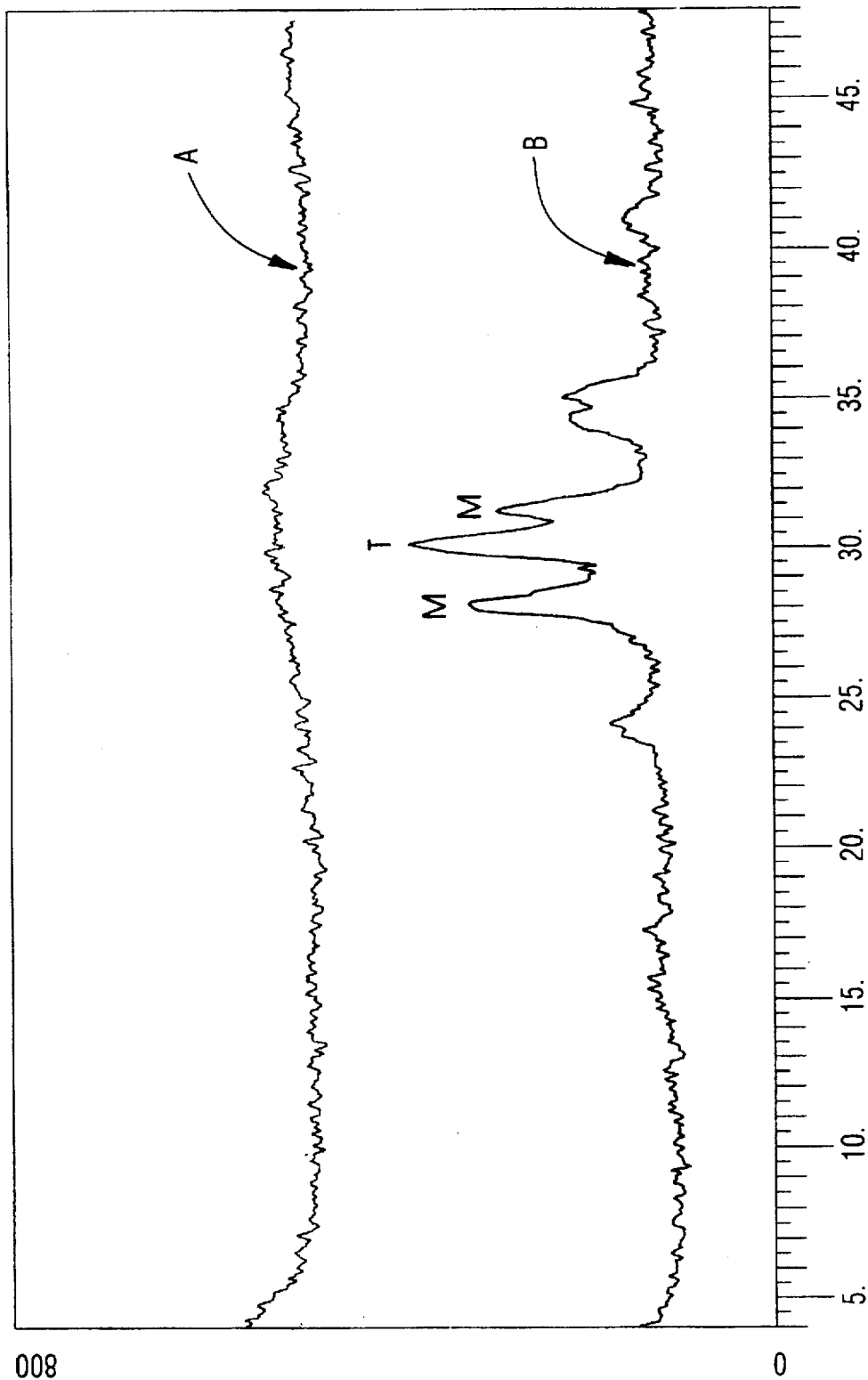
FIG. 1 is an X-ray diffractogram of the material disclosed in Example 1.

"Carbonylation of an arylene to an arylaldyde (e.g., toluene to tolualdehyde)" refers to the following chemical reaction:

The reactants may be in either the gas phase or the liquid phase. The reaction may be run either batchwise or continuously. While the reaction is preferably directed to the carbonylization of toluene to tolualdehyde, it is applicable to the carbonylation of any arylene to an arylaldehyde.

"Source of carbon monoxide" refers to any source of carbon monoxide for the carbonylation reaction. For example, synthesis gas is a source of carbon monoxide. Synthesis gas refers to any of several gaseous mixtures that are formed by reacting carbon-rich substances with steam, or steam and oxygen. Synthesis gases contain carbon monoxide and hydrogen. A preferred synthesis gas is H$_2$/CO.

"Heterogeneous system" refers to a catalytic reaction in which the reactants and the catalyst comprise two distinct phases, e.g. gases over solids, or liquids containing finely divided solids as a disperse phase. A heterogeneous system is distinct from a homogeneous system. A homogeneous system refers to a catalytic reaction in which the reactants and the catalyst comprise only one phase, e.g. an acid solution (liquid) catalyzing other liquid components.

"Being essentially free of hydrogen chloride" means that hydrogen chloride gas in equimolar ratio to the carbon monoxide is not necessary in the instance reaction. Preferably, no hydrogen chloride gas is added to the reaction.

"Solid acid catalyst" refers to a solid substance that affects the rate of selectivity of a chemical reaction through a reaction pathway that involves either Lewis acid or Brönsted acid sites present on the solid surface. The preferred solid acid catalyst comprises a zirconia support containing at least 0.1% wt. of catalyst sulfur and a metal promoter adapted for activating the carbon monoxide or a source of carbon monoxide (the metal promoter is discussed below). The sulfonated zirconia, manufacture of same is illustrated in the appended examples, is the source of the Lewis acid and Brönsted acid sites. The sulfonated zirconia, which is made by calcination in air at temperatures above 500° C., is a mixture of tetragonal (T) and monoclinic (M) zirconia. The molar ratio of T/M is preferably greater than 1.

"Capable of sorbing . . . on Brönsted acid sites" refers to the number of Brönsted acid (proton donor) sites per weight of catalyst. It is measured by FT-IR of chemisorbed pyridine. Raw measurement data was converted using the integrated molar extinction coefficient (IMEC) for Brönsted acid on Si/Al catalysts of 1.67 $cm^2$/mmole. In the instant invention, it is at least 0.01 mmole pyridine/gram catalyst. Preferably, it is greater than or equal to 0.1 mmole pyridine/gram catalyst.

"Capable of sorbing . . . Lewis acid sites" refers to the number of Lewis acid (electron acceptor) sites per weight of catalyst. It is measured by FT-IR of chemisorbed pyridine. Raw measurement data was converted using the integrated molar extinction coefficient (IMEC) for Lewis acid on Si/Al catalyst of 2.22 $cm^2$/mmole. In the instant invention, it is at least 0.01 mmole pyridine/gram catalyst. Preferably, it is greater than or equal to 0.1 mmole pyridine/gram catalyst.

"A metal promoter adapted for activating the carbon monoxide or the source of carbon monoxide" refers to a metal capable of reversibly binding carbon monoxide. Such metal promoters may be selected from the group of transition metals, lanthanides, actinides, and combinations thereof. Preferably, it is the transition metals consisting of the Group VI, VII, VIII, or IB metals. Examples of the transition metals include: Fe, Mn, Cu, Co, Mo, Ir, Cr and combinations thereof. Most preferred are Cu, Fe/Mn, and Cr. The metal promoter should comprise at least 0.1% by weight of catalyst. The molar ratio of iron to manganese should range from 0.1 to 10, preferably 1.0 to 5.0, and most preferrably 1.5 to 3.0.

"Surface area" of the solid acid catalyst refers to the actual surface area (typically in square meters) that a sample of catalyst possesses per unit weight of catalyst (typically in grams). Surface area measurement is discussed below. In the present invention, the surface is greater than or equal to about 10 $m^2$/g. Preferably, it is greater than or equal to about 100 $m^2$/g.

The ratio of catalyst to reactant (toluene) is in the range of about 0.001 to 1 g catalyst per 1 g toluene. Preferably, the ratio is about 0.04 to 0.06 g catalyst to 1 g toluene.

The ratio of CO or $H_2$/CO to toluene is in the range of about 15:1 to about 30:1. Preferably the ratio is about 20:1.

The carbonylation reaction temperature may range from about –40° C. to about 200° C. Preferably, the temperature ranges from about 0° C. to about 100° C. Most preferably, the temperature ranges from about 30° C. to about 60° C.

The carbonylation reaction pressure may range from about 20 psig to about 4000 psig. Preferably, the pressure ranges from about 20 psig to about 200 psig. Most preferably, the pressure ranges from about 20 psig to about 40 psig.

Further details about the invention are illustrated with reference to the non-limiting examples set forth below.

Surface area measurements were made with an ASAP-2010 nitrogen porosimeter from Micrometrics Corporation. Prior to testing, samples were degassed under vacuum at 400° C. for 4 hours.

Metal levels on catalysts were measured by atomic absorption spectroscopy.

Pore saturation, discussed in the examples below, refers to a single step procedure where sufficient liquid is added to completely fill the pore volume of the catalyst without further wetting the catalyst surface.

Preparation of Sulfated Ziconia

EXAMPLE 1

A solution of 20% wt. $ZrOCl_2$ in water was dropwise titrated with 10% wt. $NH_4OH$ at 40° C. with vigorous agitation until the solution pH reached the value of 6.0. After overnight aging at room temperature (25° C.), the precipitate (crystals of $Zr(OH)_4$) was separated from the liquid by a centrifuge and washed with water at about 70° C. The washed precipitate was allowed to dry at 200° C. for 10 hours. The X-ray diffractogram in FIG. 1 indicates that the material was amorphous. In FIG. 1, A is the dryed material; and B is the calcined material; M refers to monoclinic; and T refers to tetragonal. Its surface area was 237 $m^2$/g. On calcination (540° C. for 10 hour in air), the precipitate crystallized into a mixture of monoclinic (M) and tetragonal (T) zirconia ($ZrO_2$).

Preparation of Catalyst

EXAMPLE 2

The dried zirconia prepared in accordance with Example 1 was pore saturated with a 20% (v/v) $H_2SO_4$ solution to generate a solid containing about 1% S. Essentially all of the sulfur in $H_2SO_4$ is incorporated into the catalyst sample, allowing for stoichiometric pore saturation. After calcination at 540° C. for 10 hours, the amorphous material crystallized preferentially into tetragonal $ZrO_2$ and had a surface area of 95 $m^2$/g.

EXAMPLE 3

The material in Example 1 is pore saturated repeatedly using a 20% (v/v) $H_2SO_4$ solution to generate a sulfated zirconia containing about 4.4% S. This material upon calcination at 540° C. for 10 hours to form a predominately tetragonal $ZrO_2$ and had a surface area of 154 $m^2$/g.

EXAMPLE 4

The dried zirconia described in Example 1, was pore saturated with a solution prepared by dissolving $Fe_2(SO_4)_3 \cdot 5 H_2O$ crystals in water to generate a solid containing approximately 4.4% S, 3% Fe. After drying at 120° C./10 hours and calcination in air at 540° C. for two hours, the iron impregnated $ZrO_2$ had surface area of 196 $m^2$/g and contained a tetragonal $ZrO_2$ phase.

EXAMPLE 5

The dried zirconia described in Example 1 was pore saturated with a solution prepared by dissolving $MnSO_4 \cdot H_2O$ crystals in water to generate a solid containing approximately 1.2% Mn. After drying at 120° C./10 hours and calcination in air at 540° C. for 2 hours, the manganese impregnated $ZrO_2$ had surface area of 180 $m^2$/g and contained a tetragonal $ZrO_2$ phase.

EXAMPLE 6

The dried zirconia described in Example 1 was pore saturated with a solution prepared by dissolving $Fe_2(SO_4)_3 \cdot 7 H_2O$ and $MnSO_4 \cdot H_2O$ crystals in water to generate a solid containing approximately 4.4% S, 3% Fe and 1.2% Mn. After drying at 120° C./10 hours and calcination in air at 540° C. for 2 hours, the metal impregnated $ZrO_2$ had a surface area of 82 $m^2$/g and contained a tetragonal $ZrO_2$ phase.

EXAMPLE 7

The dried support from Example 1 was pore saturated with $CuSO_4 \cdot 5H_2O$ in 20% $H_2SO_4$ solution, to place about 3% Cu on the support. The dried (200° C./10 hours) Cu loaded sulfated zirconia had a surface area of 132 m²/g.

EXAMPLE 8

The dried support from Example 1 was pore saturated with a mixture of $CoSO_4$ and $(NH_4)_6 Mo_7O_{24} \cdot 4H_2O$ in 20% wt. $H_2SO_4$ solution, to place Mo/Co (molar ratio)=1.8 on the support. Metal loadings of 3.0% and 1.0% by weight of Mo and Co, respectively, were obtained. The dried (200° C./10 hours) metal loaded sulfated zirconia powder had a surface area of 144 m²/g.

EXAMPLE 9

The dried support from Example 1 was pore saturated with a 20% $H_2SO_4$ solution containing both $CuSO_4 \cdot 5H_2O$ and $MnSO_4 \cdot H_2O$, to produce a catalyst having both Cu and Mn with a Cu/Mn molar ratio of 2.5. The dried (200° C./10 hours) catalyst had a surface areas of 106 m²/g.

EXAMPLE 10

The dried support from Example 1 was pore saturated with $IrCl_5$ in 20% $H_2SO_4$ solution, to produce a catalyst having about 2.5% Ir on the support. The dried (200° C./10 hours) Ir loaded sulfated zirconia had a surface area of 114 m²/g.

EXAMPLE 11

A solution of 10 grams $Zr(OH)_4$ in 55 ml of 0.3M aqueous $Cr(NO_3)_3$ solution was allowed to sit for 30 minutes after which time it was filtered, and the solid residue dried for 4 hours at 110° C. To the dried solid, 50 ml of 3% (w/w) $(NH_4)_2SO_4$ solution is added, and allowed to react for 30 minutes. This reaction mixture is then filtered, and the solid dried for 15 hours at 110° C. This second solid is then treated for 30 minutes with an additional 50 ml of 3% $(NH_4)_2SO_4$, reacted for 30 minutes, filtered and dried for 4 hours at 110° C. The resulting catalyst is dried under flowing air for 1 hour at 200° C. and calcined under air for 1 hour at 650° C. to produce a catalyst having about 1.4% (wt/wt) Cr and 1.1% (w/w) S on the support.

EXAMPLE 12

Two types of reactors were used to characterize the above described catalysts: 1) a steady-state, tubular flow reactor in which the reactants entered the vessel as a gas; and 2) a semi-batch reactor for which one reactant, CO gas, was continuously bubbled through liquid toluene during the test. For each reactor configuration, a known amount (discussed below) of powdered catalyst was confined in the reactor during the test. Both reactors were operated at nearly isothermal conditions during the testing. The following is a detailed description of each reaction environment.

Tubular flow reactor. A gas rich in carbon monoxide (CO) was contacted with liquid toluene to produce a feed gas mixture to the reactor which contained gaseous CO and gaseous toluene (about 15–30:1 CO:toluene). The temperature of this feed gas was adjusted to the desired value (0°–200° C.) by passing it through an appropriate sized furnace before the gases contacted the catalyst particles which were confined in the tubular flow reactor vessel which was also at the desired temperature of the test (0°–200° C.). The gas pressures and the flow of the gas mixture to the reactor (100–1,000 standard temperature and pressure (STP) cm³/min) and the mass of catalyst (1–10 grams catalyst) in the reactor were adjusted to the desired values so as to produce a gas hourly space time of $1.67 \times 10^{-5}$ to $1.67 \times 10^{-3}$ grams catalyst-hours/STP cm³. The pressure inside the reactor was controlled by an appropriate back-pressure regulator so as to maintain a total pressure of 0–100 psig. Products and some of the reactant (toluene) were condensed from the effluent stream by a refrigerated vessel maintained at −20° C. during the test. This partially-condensed gas was sent to a gas chromatograph/mass spectrometer for analysis and the gas flow rate was measured by a wet test meter.

Semi-batch reactor. The batch reactor was configured to allow CO-rich gas to bubble through the toluene liquid and exit the reactor during the reaction period. The reactor was filled with 50–100 cm³ of liquid toluene at room temperature and atmospheric pressure to which was added 1–5 g of solid catalyst with the preferred ratio of 0.04 to 0.06g catalyst/1g toluene. The system was pressurized 0–100 psig using the CO-rich feed gas. The reactor temperature was adjusted to 0°–70° C. for the duration of the experiment and stirred continuously. Liquid samples (1 cm³) were withdrawn periodically for analysis by gas chromatograph/mass spectrometer (GC/MS). The reactor effluent gas was directed through a refrigerated vessel maintained at −20° C. during the test. The contents of this vessel was examined by GC/MS at the conclusion of the test.

The yield of p-tolualdehyde is the mass of p-tolualdehyde produced during the test divided by the mass of toluene fed to the flow reactor or divided by the mass of toluene put in the semi-batch reactor initially. Results of toluene carbonylation by catalysts are set forth in TABLE 1.

TABLE 1

| Catalyst Example | Metals Supported | Reaction Temp °C. | p-tolualdehyde yield |
|---|---|---|---|
| 2 | None | 50 | None detected |
| 3 | None | 50 | None detected |
| 4 | Fe | 50 | None detected |
| 5 | Mn | 30 | None detected |
| 6 | Fe/Mn | 50 | 1.3% |
| 7 | Cu | 50 | 0.1% |
| 8 | Co/Mo | 50 | None detected |
| 9 | Cu/Mn | 50 | None detected |
| 10 | Ir | 50 | None detected |
| 11 | Cr | 50 | 1.7% |

The present invention may be embodied in other specific forms without departing from the spirit or essential attributes thereof and, accordingly, reference should be made to the appended claims, rather than to the foregoing specification, as indicating the scope of the invention.

We claim:

1. A process for making tolualdehyde comprising the step of:
   carbonylating, in a heterogeneous system and without the use of hydrogen chloride, toluene in the presence of either carbon monoxide or a source of carbon monoxide and in contact with a solid acid catalyst: capable of sorbing 1) at least 0.01 mmole pyridine/gram of catalyst on Brönsted acid sites and 2) at least 0.01 mmole pyridine/gram catalyst on Lewis acid sites; having 3) a metal promoter adapted for activating the carbon monoxide or the source; and 4) a surface area greater than 10 m²/g.

2. The process according to claim 1 wherein carbonylation occurs at a temperature ranging from about −40° C. to about 200° C.

3. The process according to claim 1 wherein carbonylation occurs at a temperature ranging from about 0° C. to about 100° C.

4. The process according to claim 1 wherein carbonylation occurs at a temperature ranging from about 30° C. to about 60° C.

5. The process according to claim 1 wherein carbonylation occurs at a pressure ranging from about 20 psig to about 4000 psig.

6. The process according to claim 1 wherein carbonylation occurs at a pressure ranging from about 20 psig to about 200 psig.

7. The process according to claim 1 wherein carbonylation occurs at a pressure ranging from about 20 psig to about 40 psig.

8. The process according to claim 1 wherein said catalyst further comprises:

a zirconia support containing at least 0.1% by weight of the catalyst sulfur, said support comprising a mixture of tetragonal zirconia and monoclinic zirconia such that a ratio of tetragonal zirconia to monoclinic zirconia is greater than 1.

9. The process according to claim 1 wherein said metal promoter is selected from the group consisting of copper, a mixture of iron and manganese, or chromium.

10. The process according to claim 8 wherein said metal promoter is copper of at least 0.1% weight of said catalyst.

11. The process according to claim 8 wherein said metal promoter is a mixture of iron and manganese and a molar ratio of iron to manganese is 0.1 to 10.

12. The process according to claim 11 wherein said molar ratio of iron to manganese is 0.1 to 5.0.

13. The process according to claim 11 wherein said molar ratio of iron to manganese is 1.5 to 3.0.

14. The process according to claim 8 wherein said metal promoter is chromium.

15. A process for making tolualdehyde comprising the step of: carbonylating, in a heterogeneous system and without the use of hydrogen chloride, toluene in the presence of either carbon monoxide or a source of carbon monoxide; and in contact with solid acid catalyst: capable of sorbing 1) at least 0.01 mmole pyridine/gram catalyst on Brönsted acid sites and 2) at least 0.01 mmole pyridine/gram catalyst on Lewis acid sites; having 3) a metal promoter adapted for activating the carbon monoxide; and 4) a surface area greater than 10 m²/g and the carbonylation being: at a temperature ranging from about −40° C. to about 200° C.; and at a pressure ranging from about 20 psig to about 4000 psig.

16. A process for making an arylaldehyde comprising the step of: carbonylating, in a heterogeneous system and without the use of hydrogen chloride, the arylene in the presence of either carbon monoxide or a source of carbon monoxide and in contact with a solid acid catalyst: capable of sorbing 1) at least 0.01 mmole pyridine/gram of catalyst on Brönsted acid sites and 2) at least 0.01 mmole pyridine/gram of catalyst on Lewis acid sites; having 3) a metal promoter adapted for activating the carbon monoxide or the source; and 4) a surface area greater than 10 m²/g and the carbonylation being: at a temperature ranging from about −40° C. to about 200° C., and at a pressure ranging from about 20 psig to about 4000 psig.

17. A solid acid catalyst comprising:

1) a capability of sorbing at least 0.01 mmole pyridine/gram catalyst on Brönsted acid sites;

2) a capability of sorbing at least 0.01 mmole pyridine/gram catalyst on Lewis acid sites;

3) a metal promoter adapted for activating carbon monoxide or a source of carbon monoxide; and 4) a surface area greater than 10 m²/g.

18. The solid catalyst according to claim 17 further comprising a sulfated zirconia having said Brönsted and Lewis acid sites thereon.

19. The solid catalyst according to claim 17 wherein said metal promoter is selected from the group consisting of transition metals, lanthanides, actinides, and combinations thereof.

20. The solid catalyst according to claim 19 wherein said transition metals are selected from the group consisting of Fe, Mn, Cu, Co, Mo, Ir, Cr, and combinations thereof.

21. The solid catalyst according to claim 17 wherein said metal promoter is Cr.

22. The solid catalyst according to claim 17 wherein said metal promoter is Fe/Mn.

23. The solid catalyst according to claim 17 wherein said Brönsted acid sites are capable of sorbing greater than or equal to 0.1 mmole pyridine/gram catalyst.

24. The solid catalyst according to claim 17 wherein said Lewis acid sites are capable of sorbing greater than or equal to 0.1 mmole pyridine/gram catalyst.

25. The solid catalyst according to claim 17 wherein said surface area is greater than or equal to 100 m²/g.

* * * * *